US011772000B2

(12) United States Patent
Barcias

(10) Patent No.: US 11,772,000 B2
(45) Date of Patent: Oct. 3, 2023

(54) USER INTERACTION SELECTION METHOD AND APPARATUS

(71) Applicant: Sony Interactive Entertainment Inc., Tokyo (JP)

(72) Inventor: Jesus Lucas Barcias, London (GB)

(73) Assignee: Sony Interactive Entertainment Inc., Tokyo (JP)

( * ) Notice: Subject to any disclaimer, the term of this patent is extended or adjusted under 35 U.S.C. 154(b) by 29 days.

(21) Appl. No.: 16/921,315

(22) Filed: Jul. 6, 2020

(65) Prior Publication Data

US 2021/0016182 A1 Jan. 21, 2021

(30) Foreign Application Priority Data

Jul. 19, 2019 (GB) ...................................... 1910354

(51) Int. Cl.
*A63F 13/795* (2014.01)
*A63F 13/21* (2014.01)
*A61B 5/00* (2006.01)

(52) U.S. Cl.
CPC .......... *A63F 13/795* (2014.09); *A61B 5/6897* (2013.01); *A63F 13/21* (2014.09)

(58) Field of Classification Search
CPC ........ A63F 13/795; A63F 13/21; A63F 13/48; A63F 13/79; A61B 5/6897
USPC ........................................................ 463/42
See application file for complete search history.

(56) References Cited

U.S. PATENT DOCUMENTS

| | | | |
|---|---|---|---|
| 10,751,629 B2* | 8/2020 | Xue | A63F 13/67 |
| 10,792,577 B2* | 10/2020 | Trombetta | A63F 13/795 |
| 2012/0178529 A1 | 7/2012 | Collard | |
| 2013/0007013 A1 | 1/2013 | Geisner | |
| 2014/0187312 A1* | 7/2014 | Layne, IV | A63F 13/2145 463/24 |
| 2016/0001181 A1 | 1/2016 | Marr | |
| 2016/0144278 A1 | 5/2016 | El Kaliouby | |
| 2016/0332074 A1 | 11/2016 | Marr | |
| 2017/0065892 A1 | 3/2017 | Loeb | |
| 2018/0111051 A1 | 4/2018 | Xue | |
| 2018/0369696 A1 | 12/2018 | Aghdaie | |

FOREIGN PATENT DOCUMENTS

| | | |
|---|---|---|
| WO | 2011092549 A1 | 8/2011 |
| WO | 2015130426 A1 | 9/2015 |

OTHER PUBLICATIONS

Combined Search and Examination Report for corresponding GB Application No. 1910354.8, 7 pages, dated Jan. 13, 2020.

(Continued)

*Primary Examiner* — Michael A Cuff
(74) *Attorney, Agent, or Firm* — Matthew B. Dernier, Esq.

(57) ABSTRACT

A game selection system for matching a current user to a subsequent game session includes one or more conventional videogame controllers operable to provide data to the game selection system, one or more correlators trained to receive as a first input at least a subset of data from the one or more conventional videogame controllers, and generate as a final output data relating to the likelihood of the user quitting a game session, and a modification processor configured to modify a parameter related to matching the current user to a subsequent game session in response to the final output data.

15 Claims, 4 Drawing Sheets

(56) References Cited

OTHER PUBLICATIONS

Extended European Search Report for corresponding EP Application No. 20183236.7, 7 pages, dated Dec. 17, 2020.
Kiel Mark Gilleade, et al., "Affective Videogames and Modes of Affective Gaming: Assist Me, Challenge Me, Emote Me," ACE Proceedings of DiGRA 2005 Conference: Changing Views-Worlds in Play, URL:http://www.digra.org/wp-content/uploads/digital-library/06278.55257.pdf, 7 pages, Apr. 16, 2005.

* cited by examiner

USER INTERACTION SELECTION METHOD AND APPARATUS

BACKGROUND OF THE INVENTION

Field of the Invention

The present invention relates to a user interaction selection method and apparatus.

Description of the Prior Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Traditionally, matchmaking algorithms for games have the aim of matching players together so that the match is enjoyable. The original matchmaking algorithms were developed for chess (such as the so-called 'Elo' rating system), and are based on the assumption that an enjoyable match is one that is most likely to end up in a draw (and indeed, the phrase 'well matched' is often understood more generally to mean players with a parity of skill).

The transition to matchmaking for videogames has prompted the incorporation of other factors when considering a good match, such as environmental conditions (e.g. network bit rate and/or lag), social (for example whether users are on a mutual friend list, or in the case of play via the Internet, whether users share the same language, or other demographic features if relevant), as well as factors specific to the individual game, such as a particular desired game mode, or game requirements such as the selection of a particular class of character within a team game.

The resulting matchmaking rating algorithms thus try to provide a good match of skill between players, subject to these other practical constraints imposed by the technical nature of playing online.

However, there is significant room for improvement in these techniques.

The present invention aims to address or mitigate this issue.

SUMMARY OF THE INVENTION

In a first aspect, a game selection system is provided in accordance with claim 1.

In another aspect, a game selection method is provided in accordance with claim 14.

Further respective aspects and features of the invention are defined in the appended claims.

It is to be understood that both the foregoing general description of the invention and the following detailed description are exemplary, but are not restrictive, of the invention.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

A user interaction selection method and apparatus are disclosed. In the following description, a number of specific details are presented in order to provide a thorough understanding of the embodiments of the present invention. It will be apparent, however, to a person skilled in the art that these specific details need not be employed to practice the present invention. Conversely, specific details known to the person skilled in the art are omitted for the purposes of clarity where appropriate.

Figure 2:
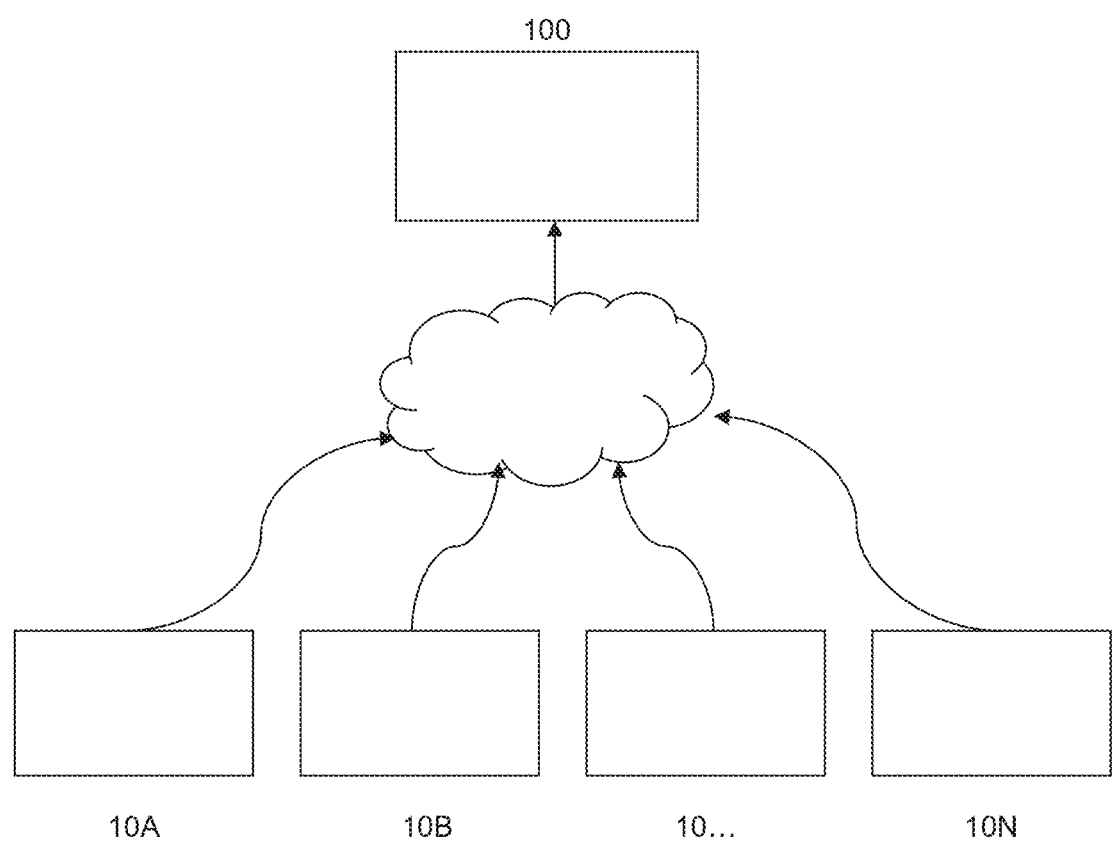
FIG. 2 is a schematic diagram of a multi-user online videogame system.

Referring now to the drawings, wherein like reference numerals designate identical or corresponding parts throughout the several views, FIG. 2 illustrates a typical multiplayer scenario, comprising an administrative server 100 (which may host the game for a plurality of players, or act to distribute information from/to a client that is hosting the game for a plurality of players). This server is connected to a plurality of client devices 10A, 10B . . . 10N, corresponding to a plurality of players A, B, . . . N. The server typically manages multiple instances of the game, in each of which a subset of the currently available players are placed, with this selection typically governed by a matchmaking algorithm so that players in one instance of the game are well matched.

In an embodiment of the present disclosure it has been appreciated however that conventional matchmaking algorithms do not take account of the time that a user spends playing, and the effect this has on their emotional response to gameplay.

Notably, multiplayer videogames are structured to have relatively short matches (by way of nonlimiting example, in the order of 5 to 30 minutes duration). Hence in the equivalent amount of time it may take to play a single game of chess, a user may play a number of videogame matches.

As an example, in a multiplayer videogame a first user A is matched with user B, as both have the same skill level, and this results in a very intense match (e.g. one that tends to end in a draw), so that both players enjoy the experience. After that match, user A is then matched with user C, who again has the same skill level, and the match is intense again. After that, user A is paired against user D, who again has a similar skill level, resulting in other intense match.

However, over time user A will become tired; intense matches require concentration, dexterity and stamina. As a result whilst user A may still play to a high level of skill in each match, doing so requires gradually more effort, and each match becomes gradually less enjoyable. However the matchmaking algorithm will continue to pit user A against other users with the same skill level.

In reality, user A really just want a more relaxed game, but is left with the options of either continuing to work hard to beat skilled players or (depending on the game) risk losing their skill rating by losing, or just quitting play altogether. Neither outcome is satisfactory.

Accordingly, the present invention seeks to detect when a given player is becoming tired of playing to their current level of skill, and modify a matchmaking algorithm accordingly.

A user's tiredness may express itself in a variety of ways, but particularly in terms of being frustrated (for example because fatigue means they are unable to maintain a desired level of skill), or in terms of boredom (for example because fatigue means they are no longer stimulated by the game), and hence more generally in terms of their immersion/engagement (for example the user's extent and nature of engagement with the game) or conversely their disengagement.

Meanwhile a user's enjoyment of the game can either be inferred from a lack of indicators of tiredness as described above, or from direct positive indicators of enjoyment, as described later herein.

Hence more generally, a user can have a positive or negative degree of immersion with matches of the current skill level, with negative immersion arising from tiredness or fatigue, frustration, boredom, lack of immersion or the like.

A problem with this approach however is how to measure negative immersion arising from frustration, boredom, tiredness, or indeed positive immersion arising from enjoyment, using the conventional inputs provided by conventional videogames consoles.

These conventional inputs may be placed in two classes. First class captures direct qualities of the user without direct connection to the user, and include a video camera, which can capture one or more of the user's face and body, and hence also their expression, pose, and/or movement, and a microphone which can counter the users speech and exclamations.

The second class captures commands issued by the user through some form of direct connection to the user (even if this connection is transitory, as in the press a button). Examples include a handheld videogame controller such as the Dual Shock 4 ® (DS4) or PlayStation Move®, or the PlayStation VR headset or head mounted display (HMD). These three particular examples also represent transition from an emphasis on button input to an emphasis on motion input; the DS4 comprises a plurality of input buttons and joysticks, as well as motion tracking means, but typically the majority of inputs are provided through the buttons and joysticks. The PlayStation Move also comprises a plurality of input buttons and can comprise a joystick, but these buttons are typically used in conjunction with physical movement of the controller as an active mode of input (for example, point with the Move and shoot with a button). Finally the HMD may not include any play related inputs, and rely instead on the placement, direction and movement of the user's head, optionally in conjunction with some other videogame controller such as the DS4 or Move.

These conventional inputs are referred to as conventional because they already exist as commonplace peripherals for one or popular videogame consoles.

Alternatively, one may place conventional inputs into two other classes. In this case a first class represents bundled inputs (i.e. those assumed to be available for every console of a particular type). Typically this corresponds only to the handheld videogame controller, such as the DS4.

The second class then corresponds to optional conventional inputs, which typically includes the likes of the PlayStation Move and PlayStation VR headset.

Notably, none of these conventional inputs comprise the additional functionality of a dedicated or specific biofeedback sensor.

Biofeedback sensors enable some form of physiological assessment of the user's state; typical sensors may provide heart rate and/or electrocardiograph monitoring, skin galvanic response or electrodermal activity detection, respiratory rate/depth detection, brainwave or electroencephalography detection, electromyography (muscle stimulation) detection, and the like.

These can be distinguished from conventional videogame controllers, which are designed to capture actions of the user generated intentionally to command the videogame console. As noted above, these can be limited to hand movements (pressing buttons, pulling triggers, pushing joysticks) on a handheld controller, and/or may incorporate gestures (such as pointing a move controller or moving it in a predetermined pattern), and/or may incorporate whole-body movement (for example to duck under a virtual obstacle by moving the user's head down when wearing an HMD).

It would be useful therefore to augment the control of a videogame using conventional videogame controllers (whether bundled or optional) with one or biofeedback sensors so that data indicative of the physiological state of the user (and in particular whether they were tired, bored, frustrated or exhibiting any other indication of negative immersion that may lead the user to disengage from play) could be determined, and an improved matchmaking algorithm could adapt in response accordingly.

However, existing users of any particular videogame console are unlikely to wish to purchase one or more dedicated biofeedback sensors, partly due to the cost, and partly due to the expectation that only a limited number of games would support any optional and new peripheral of this type. Similarly, existing developers of games for a particular videogame console are unlikely to structure gameplay and matchmaking around the functionality of one or more dedicated biofeedback sensors that they expect very few users will buy. These expectations will be compounded if the proposed use related to matchmaking, where it may be anticipated that both parties in any given match may need to have the biofeedback sensor equipped, making the odds of the best use of the peripheral significantly lower still. Consequently both parties unwittingly conspire to fulfil their negative expectations.

As a result, it is not practical to expect users or developers to rely on biofeedback sensors to determine their emotional state during multiplayer gameplay.

However in embodiments of the present disclosure, it has been appreciated that a user's voluntary and/or involuntary inputs to conventional videogame controllers can also be influenced by their emotional state; nevertheless, the relationship between these influences on conventional inputs and an emotional state of a user can be complex and multivariate, and may potentially be different for different players (for example to a first approximation between players of different personality types).

Accordingly, to help to model the relationship between a user's interaction with a conventional controller and their possible emotional state, in an embodiment of the present disclosure a first correlator is trained to relate one or more inputs from a conventional controller to data from one or more biofeedback sensors.

The raw and/or processed inputs from one or more conventional controllers and the raw and/or processed data from the one or more biofeedback sensors are collected at the same time from each of one or more, and typically a statistically significant cohort, of test subjects (for example, volunteers, QA testers, alpha or beta testers, or the like), who are each provided with the relevant biofeedback sensor equipment for the purpose of training such a first correlator.

In addition, optionally data from the game or calibration/testing application used for the purposes of training the first correlator may also be recorded. This may provide additional contextual data of use to the first correlator (for example relating to variability of timing of response in relation to game/application events, and determining whether inputs are likely to be intentional or unintentional, or responsive to events in the game/application or user originating events).

The first correlator itself may be any suitable mechanism for determining correlations between multiple inputs and multiple outputs. A typical example may be any suitable machine learning system, such as for example a neural network, which is provided as an input with at least a subset of raw and/or processed inputs from at least a subset of the or each conventional controller used by at least a subset of the test subjects, and provided as a target/output with at least a subset of raw and/or processed data from at least a subset of the or each biofeedback sensor used by the at least subset of test subjects.

The input may thus include for conventional and bundled controllers, by way of nonlimiting examples, button presses, joystick activations (for example indicative of extent and direction of joystick activation), trigger activations (for example indicative of extent of activation), and motion of the controller (for example indicative of how the controller is being handled, typically comprising a combination of voluntary and involuntary movements), and system level buttons such as a pause button, option button, share button, operating system interrupt button or the like (typically indicative of the user wishing to at least temporarily break out of the game/application).

Notably, the input thus relates to intentional (and potentially unintentional) usage (and/or handling) of the controller during normal play. It might not, however, include inputs or input sequences that lead to quitting the game itself (for example by pressing a button that causes the user to leave gameplay and either enter a game menu that is not part of the play mechanic, or enter a system menu). It will be appreciated that the purpose of the system is to predict such an event, rather than respond after it has happened.

Similarly the input may thus include for optional controllers, by way of nonlimiting examples, button presses, joystick activations, trigger activations, controller positioning and motion of the controller (for example the execution of specific gestural movements signifying an input), image tracking (for example based on processing of a captured image of the controller or HMD) or the like.

Again similarly for controllers that capture direct qualities of the user without direct connection to the user, such as cameras and microphones the input may thus include, by way of nonlimiting examples, pose data, skeletal model data, head position and/or orientation, eye gaze direction, blink rate, facial expression, vocalisation, keyword detection and the like.

It will be appreciated that different first correlators (for example your networks for the machine learning systems) may be trained for the different classes of conventional controller. Hence a first correlator may be trained only on the bundled controller type, only on one specific optional controller type or a combination of optional controller types, or a combination of the bundled controller type and one or specific optional controller type, or only on one controller that captures direct qualities of the user without direct connection to the user, or a combination of such a controller with anyone of the bundled controller type or optional controller types.

For simplicity of explanation, training and use based on the bundled controller type (for example the Dual Shock 4) is described herein, whilst optional variations based on other controller types described above are mentioned as appropriate.

In conjunction to the above control inputs, as noted above optionally the input to the first correlator may also include timing information. This may simply be the individual timings of an input, or may be the timing of an input relative to a particular event within the game/application (for example where a particular event is expected to elicit a particular response provided through a particular input, then the relative timing of that input and possibly also any characteristic quality of that input, such as frequency, rate, degree of activation etc., may be influenced by the user's emotional state and emotional response to that event).

Consequently the input to the first correlator may comprise data characteristic of one or more of the type and quality of input made by the user, the timing of such input, optionally with respect to in game/application events, and also potentially qualitative and/or quantitative data relating to in game/application events; it will be appreciated that a sudden noise or appearance of an enemy within a game is likely to elicit a different response to a friendly wave or the gradual approach of an ally. Such events may be marked up with suitable qualitative and/or quantitative values within a test sequence for the purposes of training.

As noted above the outputs or targets of the first correlator may comprise raw or processed biofeedback data, from one or more sensors of the types discussed previously herein, or any other suitable biofeedback sensor.

Over the course of training, the first correlator identifies features of the input that correlate with features of the output/target, typically by forming a mapping between them as a consequence of this correlation influencing the training process. Specific techniques for training first correlators/neural networks/machine learning systems are well known and not discussed further here, other than to note that typically they generate an internal transform function between inputs and target outputs such that inputs that have a high correlation with a target output during training will elicit an output similar to the target during subsequent use when presented with such an input.

In this way, the first correlator can identify properties of the conventional control inputs and optionally any other contextual data provided as input to the first correlator, and use this to generate approximations of the biofeedback data that has significant correlations with these properties of the conventional control inputs.

Subsequently, the first correlator can be used in conjunction with a conventional set of equipment by a normal user to generate virtual biofeedback data corresponding to that associated with such conventional inputs during the training process, when the additional biofeedback equipment was also used.

For example, if during training a game provides a jump scare (for example, a loud bang or the sudden appearance of a monster), the user may involuntarily move the controller as part of a jolt in reaction to the scare. Such a move typically has properties different to those of an intentional movement, being of shorter duration and having higher acceleration; it is also typically predominantly vertical in direction, and the motion is substantially reversed back to the original playing position almost immediately. As such it is potentially identifiable as an involuntary jolt. In addition, raw or processed data from biofeedback sensors attached to the user is being provided as a target for the first correlator, and in response to the jump scare, one or more of an electrocardiograph signal, electrodermal signal, electroencephalography signal, electromyography signal, and/or respiratory signal, or any biofeedback data derived from any one or more of these, may change in a characteristic manner in response to the stimulation.

Hence subsequently, when a similar jolt is encountered using just the conventional controller, a trained first correlator may output data and/or signals representative of one or more of the biofeedback sensors that are characteristic of a response to that stimulation.

The real biofeedback data (and optionally virtual biofeedback data) may then similarly be used to identify the user's emotional state with respect to their enjoyment of the game and/or their likelihood of quitting if the next match provided for them is deemed unsuitable.

For example a high heart rate (or for example involuntary motions of the controller correlating with a high heart rate and so generating a virtual high heart rate from a trained first correlator) may be indicative of frustration if it occurs in between game sessions, when there is no specific stimulation been provided by the game/application. Conversely a low heart rate (or for example a lack of the voluntary motion of the controller, or delay in voluntary motion/interaction with the controller, correlating with a low heart rate and so generating a virtual low heart rate from a trained first correlator) may be indicative of boredom with it occurs during a game session when specifics stimulation is are being provided by the game/application.

The relationship between the real or virtual biofeedback data and the emotional state of the user may in principle be characterised by rules or heuristics, or alternatively the correlations between these may be determined by training a second correlator.

In this case, the second correlator can be trained using at least a subset of the real biofeedback data (and/or virtual biofeedback data) as input. The second correlator may for example be initially trained using real biofeedback data, and subsequently partially retrained using the virtual biofeedback data to tune and/or generalise the second correlator to this potentially approximate or noisy version of the original data. Optionally, second correlator can also use at least a subset of the inputs provided to the first correlator (e.g. inputs from the controller and/or game context) so that any correlations with the targets of the second correlator that are not evident in the virtual biofeedback data may also be captured by the second correlator. Optionally the subset of inputs may be small, such as for example the selection of buttons unrelated to gameplay such as to pause or accessing the operating system, which may be strongly indicative of dissatisfaction and disengagement, (or for example to share or stream content, which may be strongly indicative of enjoyment), or particular in-game events.

Meanwhile in this case the second correlator can be trained on any suitable target data indicative of the emotional state of the user that is relevant to the general aim of keeping the user enjoyably immersed in game play.

Hence the target data may relate to likelihood of being frustrated, bored, tired or the like, or alternatively or in addition more generally their degree of immersion with matches at the current skill level.

During training of a second correlator, this immersion may be determined through explicit user feedback, such as a satisfaction rating with the previous match, and/or through user behaviour, such as whether the user quits play at the end of the current match for which input data is provided, or quits play at the end of the next match (or potentially the second or third match thereafter). Optionally, users may be subsequently asked to provide a reason why they quit, so that more informative time data may be used—such as a likelihood of subsequently quitting due to fatigue, a likelihood of subsequently quitting due to frustration, or a likelihood of subsequently quitting due to boredom.

Hence during the training phase, real and/or virtual biofeedback data and optionally controller input data during gameplay may be used as an input to the second correlator, and information relating to whether or not and optionally why a user quits at the end of the next session (or optionally the end of this session, or in two or three sessions time) may be used as the target.

Taken over a corpus of players, the correlator will thus develop an internal model of the correlations between input biofeedback data (and optionally controller input data) and the likelihood of a user quitting after the next match (based on unaltered matchmaking settings), and optionally forecasting the likelihood of the user quitting after two or three matches (in order to develop a long-range forecast of user dissatisfaction rather than wait until user disengagement is imminent), and optionally why; similarly the correlator can forecast the likelihood of the user quitting after the current session (e.g. before a new match commences).

As noted above, as a variant, user feedback on one or emotional states may be used as the target, which in turn may be related to the likelihood of a user quitting using rules or heuristics as described above and again the estimated emotional state(s) may optionally be used to indicate the reason why the user quits.

Hence the system's trained output can indicate user dissatisfaction (whether directly in the form of a likelihood of quitting, and/or as an emotional state that can be related to the likelihood of quitting).

In either case, the trained second correlator has thus learned to estimate the user's emotional state or immersion as expressed through the proxy of the likelihood of quitting the game (either at the end of the current session or shortly thereafter, and optionally for a specific emotionally driven reason), based upon virtual biofeedback data output from the trained first correlator, which learned how real biofeedback data corresponds to input data from conventional controllers of one or more classes, as described previously herein.

As a result, the trained system can estimate the user's emotionally driven likelihood of continued play based on biometric feedback, but only using conventional controllers and without the use of specific biometric feedback hardware.

Given the estimation of the likelihood of the user quitting the game, a system may respond accordingly.

If the likelihood of a current user quitting the game after the next match (based on unaltered matchmaking settings) exceeds a given threshold, then the matchmaking settings may be adjusted in any one of a number of suitable ways.

Firstly, the effective skill level of the current user may be temporarily reduced, or scaled down, for the purposes of matchmaking so that the user is paired up with a less skilled player; this should result in a satisfying win for the current user and typically some respite with regards to the intensity of gameplay. The degree of reduction or downscaling may be made proportional to estimated likelihood of a user quitting, so that if it is considered that a user is very likely to quit, then they may be given a very easy opponent.

It will be appreciated that this policy can affect the satisfaction of the opponent, who is matched against a potentially more skilled player; however it will be appreciated that the proportion of significantly mismatched pairings generated will be relatively small, as this is only done when a particular user is showing dissatisfaction indicative of imminent departure from the game. In addition, a flag may be associated with the user so that they are only eligible to be selected for a match in this way once per session or predetermined time period, such as per day or per week. Alternatively or in addition, the current user may be matched to a bot (a computer-controlled opponent) of the desired skill level; this bot may optionally be presented in a similar manner to a normal user.

Secondly, the current user may be provided with a scenario that may be potentially less stressful as part of the matchmaking process; for example games often appear to randomly select the next environment/game mode for a match, but this selection may instead be made purposeful. In the case of frustration for a user, particular environment maps may be associated with lower degrees of stress, or may encourage less frenetic gameplay. Conversely for bored players some environment maps may increase stress or frenetic gameplay, etc. Similarly, different modes of play may be more or less stressful, for example team death match, free for all death match, capture the flag, and tower defence modes etc., may be judged to have different levels of stress, frustration etc., and may be chosen accordingly. Similarly, different character classes/in-game roles may have different levels of stress; switching from a melee fighter to a sniper may reduce stress; meanwhile switching from a sniper to a melee fighter may reduce boredom.

Hence it will be appreciated that this approach applies more generally for the purposes of subsequent game selection, e.g. for selecting easier bots (rather than human opponents), or a different map that attracts different types of player or play, or a different mode of play, character class, or the like; typically to reduce fatigue/stress (e.g. by making games easier/calmer) but potentially to combat boredom (e.g. by making games tougher/more frenetic).

Similarly if a likelihood of a current user quitting the game in two or three matches' time reaches a respective threshold, then again the effective skill level of the current user may be temporarily reduced or scaled down, but typically to a lesser degree than in the case of predicting that the user will quit after the next match. In this way, the intensity and emotional drain of gameplay can be gracefully reduced to track the users own fatigue, or, see can be gradually ramped up to maintain a user's interest, depending on the circumstances.

Meanwhile, if there is a likelihood of the current user quitting the game immediately after the current match, then in addition to any subsequent modified matchmaking described previously herein, the game may intervene to suggest to the user that they try something different (for example whilst presenting scores related to the current match, or during a countdown timer towards the end of the current match) so that the user is still sufficiently engaged to consider the suggestion. For example in the case of tiredness or frustration, the game may suggest playing in a tutorial mode, a solo mode, or a bonus mode, or playing a friendly match or entering a 'joke' mode (for example where shooting a player causes an amusing effect rather than a fatality, or where gravity is reduced by 90%, etc.,) so that the user is presented with an enjoyable diversion which is notionally decoupled from any sense of progress or urgency that the user may be feeling with regards to their progress in the conventional game.

It will be appreciated that there will be players whose natural playing behaviour is either very aggressive or very relaxed, and so may be continually predicted to be on the verge of quitting; upon detecting this for such users, the likelihood thresholds for changing the matchmaking process or providing other mitigating behaviours may be successively increased until the rate of triggering of mitigating actions for these users is within normal expectations. Alternatively, in these cases the above techniques may be suspended for such users.

More generally in this regard, there is likely to be a spectrum of different emotional responses (and corresponding immersion or lack thereof, and hence likelihood of quitting) amongst a population of users.

For example, when faced with a similar adversity, some players may become despondent, acting more passively, with lower reaction times, or a tendency to not try to get optional but valuable items in the game, for example. meanwhile others may become annoyed, and use repeated high-impact behaviours (such as a repeated punch action), even where this is not the most efficient choice of action.

To a first approximation, the second correlator may identify traits associated with these responses within the virtual biofeedback, and optionally some input and/or game data, and make appropriate predictions regarding the user's likelihood of quitting.

However, to a second approximation, different versions of the second correlator may be trained to model different personality types: these types may be identified either by questionnaires given to the corpus of users who provided the combined conventional and biofeedback data, or through human observation and selection of these users into such types. Hence a first user who is frustrated but expresses this through a passive rejection of gameplay rather than exhibit the frenzied attempt to overcome an adversity shown by a second user, may each show different virtual biofeedback results, but be equally likely to quit. Subsequently the first and second users in this example may be better served by different respective second correlators.

It will also be appreciated that in principle different first correlators may also be used for different personality types, as there may be different correlations between input behaviours and biofeedback signals.

Variants

Typically, the or each correlator will be trained by a developer of the game/application, or more generally may be trained on a plurality of games by the operating system provider (for example to provide a generalised early-warning system that a user is thinking of quitting, which may be provided by the operating system or middleware of a videogame console to any game/application that interacts with this system-level service, for example through an API). Such a system is typically trained centrally, because it typically uses data from a corpus of users that is supplied back for training. However, once trained, the or each correlator may be located either centrally (as one or more instances on a server) or locally on a video game console.

If the or each trained correlator is computationally and/or memory intensive, it may be hosted on the server and receive controller input data from the console. Alternatively, however, the or each trained correlator may be hosted locally on the console. However, typically the correlator does not need to operate quickly (e.g. within the time-frame of network lag, etc), and so hosting it on the server is not likely to impair operation, but may make leave memory/computational resource available to the console.

Similarly, with so-called cloud gaming, where a user has a controller and a terminal (e.g. a smart TV), but the game is run on a server, then the or each trained correlator may also be run on that server or on an affiliated sever, in a similar manner.

The description herein recites a two-stage process in which in a first stage a first correlator is trained to associate conventional controller inputs (and optionally other inputs) with target biofeedback data in order to learn to generate virtual biofeedback data in response to conventional controller inputs (and optionally other inputs), and in a second stage a second correlator is trained to associate input biofeedback data (real and/or virtual) with an (emotionally driven) likelihood of quitting a game, in order to learn to predict how likely it is that a user will quit the game (and potentially why—frustrated, bored, tired etc), based on the virtual biofeedback data and optionally other inputs.

However, in principle a single correlator may be trained to associate conventional controller inputs (and optionally other inputs) with an emotionally driven likelihood of quitting a game.

In this case, optionally the single correlator may undergo a two-stage training process, where it is first trained with conventional controller data and also biofeedback data as inputs, and the probability of quitting (and optionally emotional indicators such as tiredness, boredom, frustration etc.,) as the target. In this case the single correlator is receiving data roughly equivalent to the input the first correlator and the second correlator described previously herein, enabling associations between control inputs and biofeedback inputs to interact within the internal representation of the single correlator in order to generate an approximation of the correct target output. Subsequently, the single correlator may be trained with only the conventional controller data, and with the biofeedback inputs fixed to a neutral value. The established internal associations between the controller data and biofeedback data that feed into the generation of the target output may then relearn to compensate for the lack of variation in the biofeedback inputs. Optionally, the second stage may be achieved by slowly rescaling the value ranges of the biofeedback inputs toward a single neutral value (equivalent to slowly reducing the contrast on an image until it becomes a uniform grey).

In other words, the first training stage boot-straps relevant features of the controller input to the target output by virtue of the association with the biofeedback signals, and the second stage then seeks to preserve the link between controller input and target output whilst removing the reliance on the biofeedback input.

The final result is substantially the same as the two correlator version described previously herein, but based on a single (potentially larger or more complex) correlator.

Figure 1:
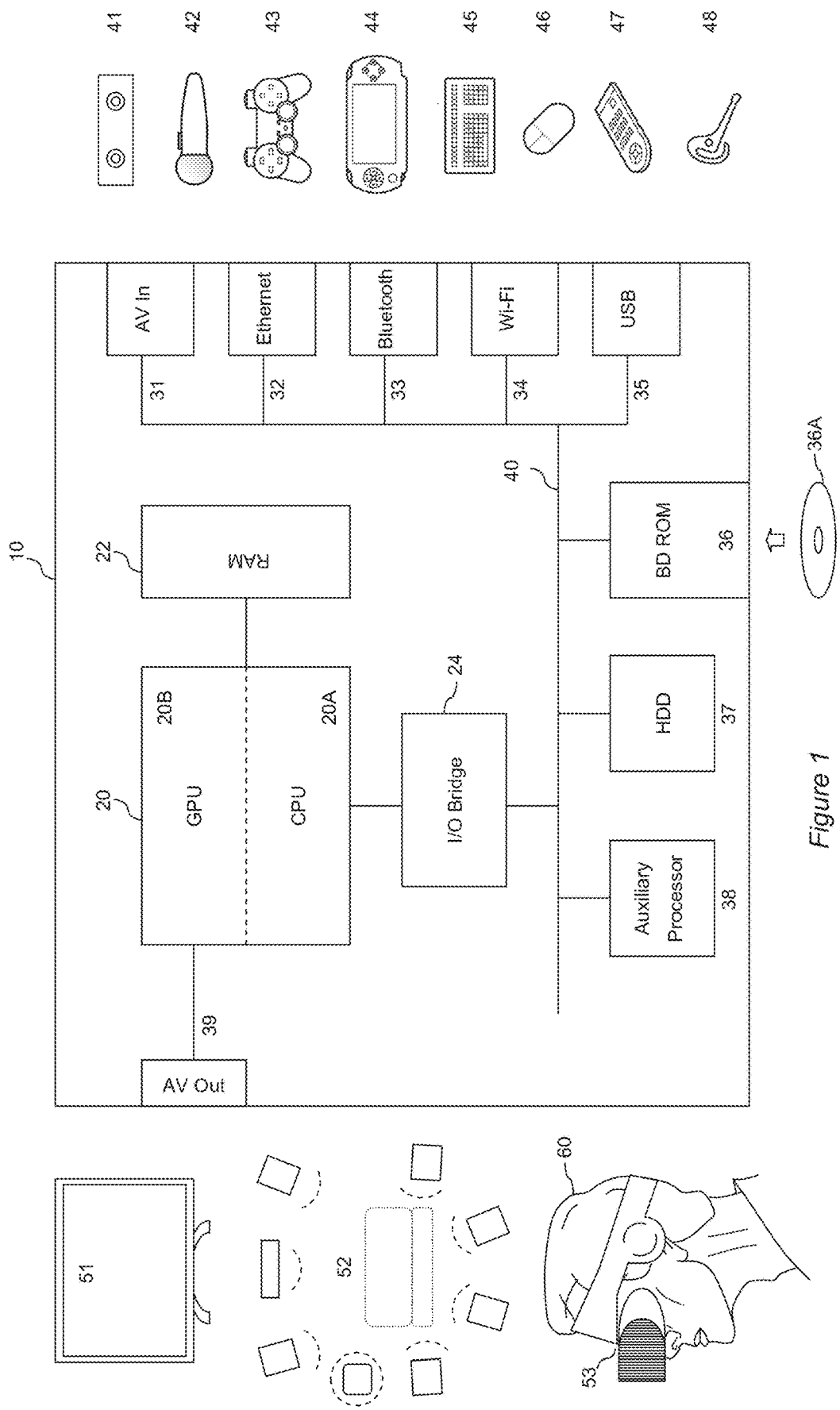
FIG. 1 is a schematic diagram of an entertainment device.
Figure 4:
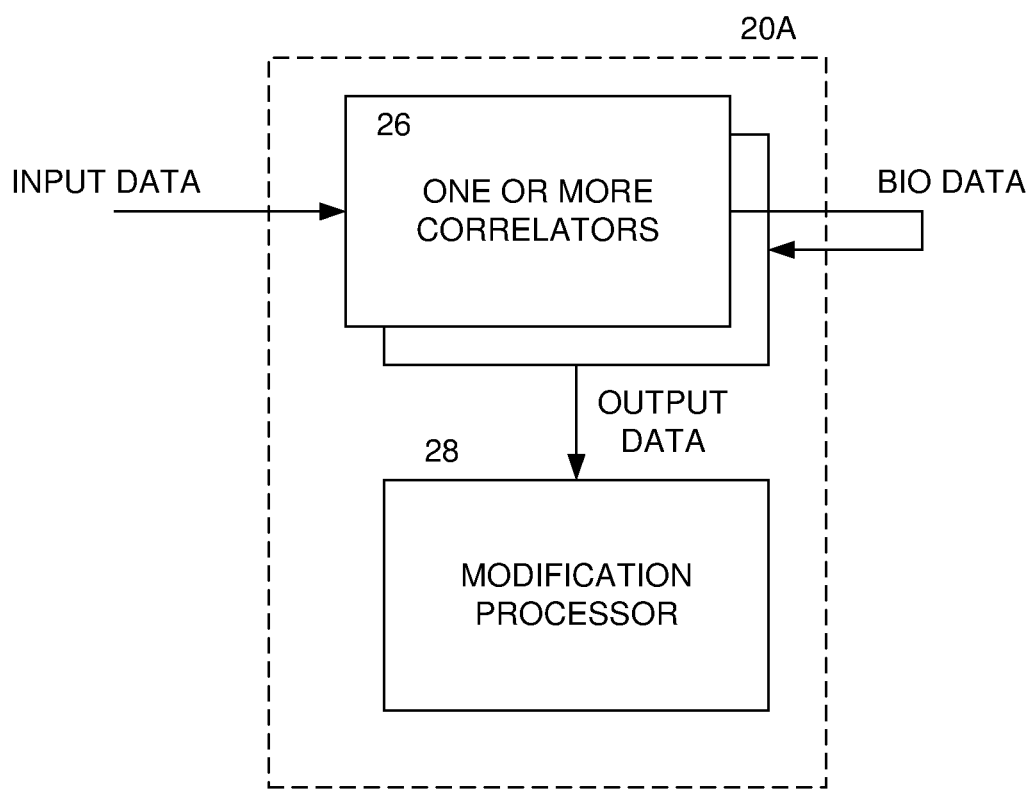
FIG. 4 is a block diagram of a data processor adapted to carry out of certain functions to achieve the game selection method in accordance with an embodiment of the present disclosure.

FIG. 4 is a block diagram of a data processor adapted to carry out of certain functions to achieve the game selection method in accordance with an embodiment of the present disclosure. In particular, the implementation shown in FIG. 4 may be achieved by way of the CPU 20A of FIG. 1 adapted to execute suitable software residing in the RAM 22. For example, the CPU 20A may implement the one or more correlators 26 and the modification processor 28 discussed hereinabove. In accordance with a specific embodiment, the one or more correlators 26 may include the first trained correlator that receives the first input data and generates the virtual biometric data; and a second trained correlator that receives as an input at least a subset of the virtual biometric data, and generates the final output data.

It will be appreciated that in addition to game selection (whether in terms of the nature of the game and/or the nature of the opponent), the system/techniques described herein may be used for other applications.

For example, the game/application developer may use the virtual biometric data and/or the final emotional data or quitting likelihood data to determine if there are problems with the user experience of their game, and modify or patch the game accordingly. Meanwhile, the user's emotional response to the game may form a characteristic pattern (for example with different response to different levels of the game, or different maps or game modes, etc), and this may enable a system to recommend new games that are likely to be enjoyed by the user, either based directly on their response to the current game (or aspects thereof) or based on the purchase and feedback behaviours of other players with similar emotional characteristic patterns.

It will be appreciated that the above methods and techniques may be carried out on conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a non-transitory machine-readable medium such as a floppy disk, optical disk, hard disk, solid state disk, PROM, RAM, flash memory or any combination of these or other storage media, or realised in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

Figure 3:
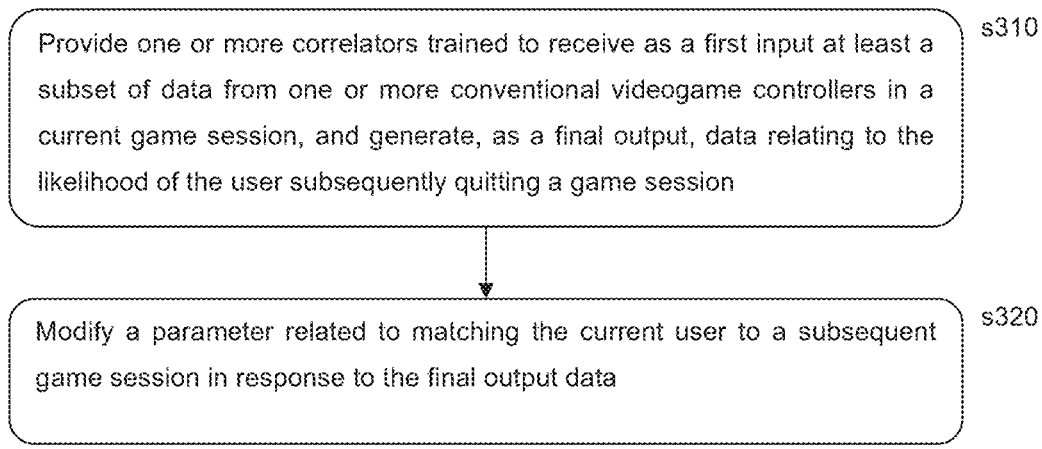
FIG. 3 is a flow diagram of a game selection method in accordance with an embodiment of the present disclosure.

Referring now to FIG. 3, in particular a method of game selection for matching a current user to a subsequent game session may comprise:

in a first step s310, providing one or more correlators trained to receive as a first input at least a subset of data from one or more conventional videogame controllers during a current game session, and generate, as a final output, data relating to the likelihood of the user subsequently quitting a game session; and in a second step s320, modifying a parameter related to matching the current user to a subsequent game session in response to the final output data.

It will be apparent to a person skilled in the art that variations in the above method corresponding to operation of the various embodiments of the method and/or apparatus as described and claimed herein are considered within the scope of the present disclosure, including but not limited to where:

one trained correlator receives the first input and generates the final output data;

a first trained correlator receives the first input and generates virtual biometric data; and a second trained correlator receives as an input at least a subset of the virtual biometric data, and generates the final output data;

the final output data indicates an estimation of one or more selected from the list consisting of the likelihood of the current user quitting a current game session, the likelihood of the current user quitting a first subsequent game session, the likelihood of the current user quitting a second subsequent game session, and the likelihood of the current user quitting a third subsequent game session;

final output data indicates an estimation of an emotional state of the current user;

the final output data indicates an estimation of the likelihood that the current user is one selected from the list consisting of tired, frustrated, and bored;

one or the conventional videogame controller is one selected from the list consisting of a handheld videogame controller, a head mounted display, and a video camera;

in response to final output data indicating a likelihood above a threshold value of the current user quitting, temporarily reducing the effective skill level of the user for the purposes of selecting the next game for the user;

in this instance, optionally the reduction in effective skill level being proportional to how soon the user is likely to quit;

in this instance, the temporarily reduced effective skill level of the user being used when selecting one or more other players as opponents;

in response to final output data indicating user dissatisfaction, the modification processor is configured to change one or more selected from the list consisting of a game map, a game mode, and a user character class;

a first correlator is trained with target biometric feedback data and corresponding conventional videogame controller input data, to generate virtual biometric data in response to conventional videogame controller input data, and a second correlator is trained with one or more from the list consisting of when a user quits the game and an emotional state of the user as target data, and one or more from the list consisting of biometric feedback data and virtual biometric data generated by the first trained correlator as input data, to generate the final output data; and a single correlator is trained with one or more from the list consisting of when a user quits the game and an emotional state of the user as target data; and conventional videogame controller input data together with biometric feedback data as input data, to generate the final output data.

The foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A game selection system for matching a current user to a subsequent game session, comprising
one or more videogame controllers operable to provide controller input data to the game selection system;
one or more trained correlators operable to receive, as a first input, first input data comprising the controller input data relating to an interaction of the current user with the one or more videogame controllers during a current game session, and generate, as a final output, final output data relating to an emotionally driven likelihood of the current user subsequently quitting the current game session based on the controller input data relating to the interaction of the current user with the one or more videogame controllers during the current game session; and
a modification processor configured to modify a parameter related to matching the current user to the subsequent game session in response to the final output data.

2. The game selection system of claim 1, comprising one trained correlator that receives the first input data and generates the final output data.

3. The game selection system of claim 1, comprising
a first trained correlator, among the one or more trained correlators that: (i) is trained to relate one or more inputs from a videogame controller to biometric data from one or more biofeedback sensors, (ii) receives the first input data comprising the controller input data, and (iii) generates virtual biometric data based on the first input data, the virtual biometric data relating to a physiological state of the current user determined without use of one or more biofeedback sensors by using only the controller input data relating to the interaction of the current user with the one or more videogame controllers; and
a second trained correlator, among the one or more trained correlators: (i) receives as an input at least a subset of the virtual biometric data, and (ii) generates the final output data based on the subset of the virtual biometric data.

4. The game selection system of claim 1, in which the final output data indicates an estimation of one or more of:
i. the likelihood of the current user quitting the current game session;
ii. the likelihood of the current user quitting a first subsequent game session;
iii. the likelihood of the current user quitting a second subsequent game session; and
iv. the likelihood of the current user quitting a third subsequent game session.

5. The game selection system of claim 1, in which the final output data indicates an estimation of an emotional state of the current user.

6. The game selection system of claim 5, in which the final output data indicates an estimation of the likelihood that the current user is one of:
i. tired;
ii. frustrated; and
iii. bored.

7. The game selection system of claim 1, in which the one or more video game controllers is one of:
i. a handheld videogame controller; and
ii. a head mounted display.

8. The game selection system of claim 1, in which, in response to the final output data indicating a likelihood above a threshold value of the current user quitting, the modification processor is configured to temporarily reduce the effective skill level of the user for the purposes of selecting the next game for the user.

9. The game selection system of claim 8, in which the reduction in effective skill level is proportional to how soon the user is likely to quit.

10. The game selection system of claim 8, in which the temporarily reduced effective skill level of the user is used when selecting one or more other players as opponents.

11. The game selection system of claim 1, in which, in response to the final output data indicating user dissatisfaction, the modification processor is configured to change one or more of:

i. a game map;
ii. a game mode; and
iii. a user character class.

12. The game selection system of claim 1, in which
a first correlator, among the one or more trained correlators, is trained with target biometric feedback data and corresponding videogame controller input data, to generate virtual biometric data in response to videogame controller input data, the virtual biometric data being indicative of a physiological state of the current user; and
a second correlator, among the one or more trained correlators, is trained with one or more of:
i. when a user quits the game; and
ii. an emotional state of the user
as target data; and one or more of:
i. biometric feedback data; and
ii. virtual biometric data generated by the first trained correlator,
as input data, to generate the final output data.

13. The game selection system of claim 1, in which
a single correlator, among the one or more trained correlators, is trained with one or more of:
i. when a user quits the game; and
ii. an emotional state of the user
as target data; and videogame controller input data together with biometric feedback data as input data, to generate the final output data.

14. A game selection method for matching a current user to a subsequent game session, comprising the steps of
providing one or more trained correlators operable to receive, as a first input, first input data comprising controller input data provided by one or more videogame controllers, the controller input data relating to an interaction of the current user with the one or more videogame controllers during a current game session, and generate, as a final output, final output data relating to an emotionally driven likelihood of the current user subsequently quitting the current game session based on the controller input data relating to the interaction of the current user with the one or more videogame controllers during the current game session; and
modifying a parameter related to matching the current user to the subsequent game session in response to the final output data.

15. A non-transitory, computer readable storage medium containing a computer program comprising computer executable instructions, which when executed by a computer system, cause the computer system to perform a game selection method for matching a current user to a subsequent game session, by carrying out actions, comprising:
providing one or more trained correlators operable to receive, as a first input, first input data comprising controller input data provided by one or more videogame controllers, the controller input data relating to an interaction of the current user with the one or more videogame controllers during a current game session, and generate, as a final output, final output data relating to an emotionally driven likelihood of the current user subsequently quitting the current game session based on the controller input data relating to the interaction of the current user with the one or more videogame controllers during the current game session; and
modifying a parameter related to matching the current user to the subsequent game session in response to the final output data.

* * * * *